United States Patent [19]

Alcock et al.

[11] Patent Number: 5,684,184

[45] Date of Patent: Nov. 4, 1997

[54] PROCESS FOR PREPARATION OF SULPHONATES

[75] Inventors: Kenneth Alcock, East Hanney; Jeremy Roger Spencer, Botley; Christopher John Adams, Tilehurst, all of United Kingdom

[73] Assignee: Exxon Chemical Patents Inc., Linden, N.J.

[21] Appl. No.: 381,972

[22] PCT Filed: Aug. 7, 1993

[86] PCT No.: PCT/EP93/02112

§ 371 Date: Apr. 6, 1995

§ 102(e) Date: Apr. 6, 1995

[87] PCT Pub. No.: WO94/04490

PCT Pub. Date: Mar. 3, 1994

[30] Foreign Application Priority Data

Aug. 14, 1992 [GB] United Kingdom .................. 9217350

[51] Int. Cl.$^6$ .................. C07C 303/02; C07C 309/31
[52] U.S. Cl. .................................................. 562/97
[58] Field of Search .................................. 562/97

[56] References Cited

U.S. PATENT DOCUMENTS 4,891,155  1/1990  Fernley et al. .................. 562/97

Primary Examiner—Joseph Conrad

[57] ABSTRACT

Sulphonates are prepared by the neutralization of a sulphonic acid with a basic hydroxide or Oxide. The process requires the staged addition of sulphonic acid to a reaction mixture comprising basic hydroxide or oxide dispersed in water/diluent mixture; the reaction mixture is basic throughout the additions of acid and at least until the point of completion of the neutralization reaction. The basic hydroxide or oxide may also be added in stages. The sulphonate product has low viscosity, low haze and good stability and is essentially chloride free as halide promoters are not utilized in the manufacture of the product.

12 Claims, No Drawings

PROCESS FOR PREPARATION OF SULPHONATES

The present invention relates to a method for the preparation of basic or neutral sulphonates and in particular to a method for the preparation of basic or neutral sulphonates which are essentially chloride free.

Basic or neutral sulphonates may be used as additives for lubricating oils such as passenger car, diesel and marine engine lubricants. Basic sulphonate additives are generally known as either low base number sulphonates or high base number sulphonates. Neutral and low base number sulphonates function primarily as surfactants, detergents and rust inhibitors. High base number sulphonates primarily function to neutralise acids produced in the oil during use. These sulphonates also help to inhibit corrosion and reduce sedimentation during use.

Neutral and low base number sulphonates for use as oil additives are usually prepared by the neutralisation of a sulphonic acid with a basic salt such as a basic calcium salt e.g. calcium oxide or hydroxide in a suitable diluent oil. The sulphonate product may be a mixture of a number of species; when calcium hydroxide is used these species may include the following:

(i) Hydrated hydroxy calcium sulphonate

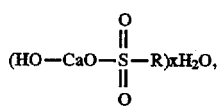

(ii) A basic calcium sulphonate

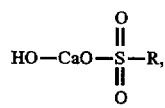

(iii) A calcium sulphonate

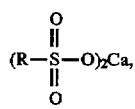

(iv) A calcium sulphonate hydrate

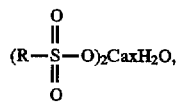

wherein R is an organic moiety and x denotes at least one molecule of water of hydration.

In addition dispersed calcium hydroxide may be present.

When preparing low base number sulphonates the basic salt is added in stoichiometric excess to that required for complete neutralisation of the sulphonic acid so that the resulting product is basic.

EP-A-135920 describes the preparation of alkaline-earth metal salts of alkaryl sulphonic acids containing from 1.5 to less than 3 wt. % water without requiring azeotropic distillation using a polar solvent and by limiting the water in the reaction mixture. Preferably the sulphonic acid is "proportioned" into the reaction mixture (i.e. added at a rate to give the required rate of salt formation). The small amount of water may be introduced as a sulphonate solution. Basic materials such as amines are added at completion of the reaction to make the product basic.

High base number sulphonates are generally prepared by a process of neutralisation and carbonation. The sulphonic acid is first neutralised with excess basic metal oxide or hydroxide in a suitable diluent. Some of the excess basic metal oxide or hydroxide is then converted to metal carbonate via carbonation. Typically the reaction is carried out in the presence of a hydrocarbon and/or polar solvents such as toluene or methanol; the solvent is subsequently removed. The resulting product is a colloidal dispersion, in a diluent oil, of sub-micron particles of $CaCO_3$ and $CaOH_2$ which are sterically stabilised by the calcium sulphonate species produced by the reaction.

Whether neutral or overbased, it is desirable that the sulphonates for use in engine lubricants should be low in sediment and/or rapidly filterable, clear rather than hazy, not unduly viscous, and stable on storage, particularly against sedimentation.

Sulphonates have been prepared from natural sulphonic acids which in turn have been prepared by the sulphonation of a suitable oil fraction with sulphuric acid. Excess sulphuric acid in the reaction mixture is neutralised with sodium hydroxide and the sodium sulphonates formed are convened to calcium sulphonates by treatment with calcium chloride. The final products contain residual chloride from the calcium chloride treatment.

Sulphonates have also been prepared from synthetic sulphonic acids which have in turn been prepared for example by the sulphonation of $C_{12}-C_{60}$ alkyl substituted benzene and/or $C_{12}-C_{60}$ alkyl substituted xylene compounds. These sulphonic acids can be used to produce sulphonates which do not have residual chloride present. It has been found, however, that some synthetic sulphonic acids cannot be satisfactorily neutralised with calcium hydroxide or lime to produce calcium sulphonates; the attempted neutralisation results in the production of gelatinous products which are solid at room temperature. Methods have been proposed to overcome this problem associated with synthetic sulphonic acids. One such method is described in GB 1 575 957 wherein a large stoichiometric excess, over that required for neutralisation of the sulphonic acid, of calcium hydroxide is added to a portion of the sulphonic acid in a diluent to produce a reaction mixture; there is a subsequent addition of the remainder of the sulphonic acid to the mixture, this addition being less than that which would be required to fully react with the remaining calcium hydroxide in the mixture. In addition a solution containing a source of chloride ion is added to the mixture after the calcium hydroxide or lime addition; the chloride ion is believed to act as promoter for the product formation and is beneficial in enabling the product of fluid, filterable products from certain sulphonic acids such as synthetic sulphonic acids. The addition of chloride promoter prevents the formation of gelatinous products. However the final product contains chloride.

The presence of chloride in calcium sulphonates and other metal sulphonates is a problem from a waste disposal and environmental point of view. Waste disposal of compositions based on chloride containing sulphonates is therefore a problem; it would be advantageous to be able to produce chloride free metal sulphonates without a loss of the beneficial properties produced by the use of chloride in their manufacture.

The present invention provides a process for the production of neutral or basic sulphonates comprising the addition of a sulphonic acid to dispersion of a basic hydroxide or oxide in a water/diluent mixture to form a reaction mixture, wherein the sulphonic acid addition is made in at least two distinct stages and such that the reaction mixture remains basic throughout the addition of the acid and at least until the point of completion of the neutralisation reaction as determined by ASTM D2896-88 discussed hereinafter.

It is preferred that the basic hydroxide or oxide is also added in two or more distinct stages, the first stage preceding the first addition of sulphonic acid, with subsequent stages preferably before the second and subsequent additions of sulphonic acid. Preferably the first addition of basic hydroxide or oxide comprises at least 50% by weight of the total basic hydroxide or oxide and most preferably comprises at least 65% by weight. The basic hydroxide or oxide is preferably a Group IA or Group IIA oxide or hydroxide though mixtures of such hydroxides and/or oxides may be used, calcium hydroxide or oxide is most preferred.

When the process is used for the preparation of low base number sulphonates it is preferred that as a neutralisation reaction aid a source of formate anion such as formic acid is added to the dispersion of basic hydroxide or oxide. This addition may be at the same time, or preferably before, the first addition of sulphonic acid. The formic acid is preferably added as an 80–90% by weight solution in water and is added in the amount of 25–35% by weight of formic acid based on total basic oxide or hydroxide used. It is preferred that the formic acid is relatively pure having a low acetic acid content, i.e. preferably less than 0.5 wt % acetic acid. It is not clearly understood how formic acid aids the neutralisation reaction; however, in addition to the aqueous dispersion of basic hydroxide or oxide a basic formate salt is formed, e.g. calcium formate when calcium hydroxide is used as the basic hydroxide. Alternatively the formic acid may be replaced by the addition of calcium formate. To introduce the same amount of formate anion, if calcium formate is used the molar amount used would be half of that used with formic acid.

The basic or neutral sulphonates produced by the process of the invention have relatively low viscosity, are essentially chloride free, have low haze values, low sediment levels and improved stability and filterability. By relatively low viscosity is meant a kinematic viscosity at 100° C. of 65 cSt or less and is preferably 50 cSt or less and most preferably in the range 30–65 cSt. By the term essentially chloride free is meant that the chloride content is 100 ppm or less and preferably 50 ppm or less.

The terms neutral, basic, low base number and high base number as used to define sulphonates should be understood in relation to ASTM D2896-88 "Standard Test Method for Base Number of Petroleum Products by Potentiometric Perchloric Acid Titration". This test method is concerned with the determination of basic constituents in petroleum products by potentiometric titration with perchloric acid in glacial acetic acid. Thus the term neutral in relation to a sulphonate is deemed to mean that no basic constituents would be detected by titrating the sulphonate by this method and the term basic in relation to a sulphonate is deemed to mean that basic constituents would be detected by titrating the sulphonate by this method. The result of this test method is quoted as a base number which is the base equivalence in mg KOH $g^{-1}$. Thus the term low base number refers to numerical values of base number which are 50 mg KOH $g^{-1}$ or less and the term high base number refers to numerical values of base number which are greater than 50 mg KOH $g^{-1}$ and may be as high as 400 mg KOH $g^{-1}$.

The process of this invention has its primary utility in producing neutral or low base number sulphonates. When formic acid or calcium formate is used in the process for preparing low base number sulphonates in conjunction with a basic hydroxide or oxide, e.g. calcium hydroxide the resulting products will have a total base number which is partly due to the presence of unreacted basic hydroxide or oxide and partly due to the presence of formate, e.g. calcium formate. It is envisaged that in some circumstances that there would be no residual unreacted basic hydroxide or oxide present and that the total base number would only be due to the presence of the relevant formate, e.g. calcium formate. It is preferred that the contribution to the total base number made by the relevant formate (which may be calculated from the amount of formate) is greater than that made by the unreacted basic hydroxide or oxide. It is preferred that the total base number of the product is not greater than 50 mg KOH $g^{-1}$ and most preferably in the range of 25 to 40 mg KOH $g^{-1}$.

The sulphonic acid may be any oil-soluble sulphonic acid and may be a natural or a synthetic sulphonic acid e.g. a mahogany or petroleum alkyl sulphonic acid; an alkyl sulphonic acid; or an alkaryl sulphonic acid. Preferably it is a synthetic sulphonic acid. The sulphonic acid may be a single sulphonic acid or a mixture of different sulphonic acids. If desired the sulphonic acid or mixture of sulphonic acids may be used in diluted form as a solution or dispersion in a diluent oil such as mineral oil, petroleum oil, or any suitable inert oleaginous material. The alkaryl sulphonic acid may be an alkyl benzene sulphonic acid or alkyl xylene sulphonic acid and most preferably is a $C_{12}$–$C_{60}$ alkyl benzene sulphonic acid or a $C_{12}$–$C_{60}$ alkyl xylene sulphonic acid and most preferably is a $C_{12}$–$C_{24}$ alkyl benzene sulphonic acid or a $C_{12}$–$C_{24}$ alkyl xylene sulphonic acid. When a mixed sulphonic acid is used it is preferred that it is a mixture of an alkyl benzene sulphonic acid and an alkyl xylene sulphonic acid. The most suitable sulphonic acids have a molecular weight of between 250 and 700 e.g. between 400–500. An example of suitable sulphonic acid mixture is a mixture of nominally $C_{24}$ alkyl benzene sulphonic acid and nominally $C_{12}$ alkyl o-xylene sulphonic acid.

The sulphonic acid is added to a water/diluent mixture in which is dispersed a basic hydroxide or oxide. The diluent may be any non-volatile, inert, oleaginous material, preferably a substantially neutral mineral or petroleum oil. It is preferred that the water/diluent mixture comprises between 1 and 50% by weight of water and more preferably between 15 and 35% by weight of water. The water reduces the viscosity of the initial water/diluent mixture. It may also aid in the promotion of the neutralisation reaction and assist in the dispersion of the added basic hydroxide and any basic salts formed during the neutralisation reaction. A low water content tends to increase the sediment content of the final product, reduce filtration rate and lower product basicity, whereas a high water content prolongs any subsequent stripping of the product and allows hydrolysis to occur with the production of flocculent material which inhibits filtration.

During the process exothermic reactions may occur. The reaction mixture temperature may be allowed to rise as a result of this, or cooling may be utilised to reduce or prevent the temperature rise. It is preferred that during the neutralisation reaction that the temperature is maintained below 100° C. and most preferably below 80° C. so that there is little or no loss of water from the mixture.

During the process a period of stabilisation may be beneficial after the first and/or the succeeding additions of sulphonic acid, to allow the neutralisation to be completed before any further additions or process stages. During a stabilisation period it may be beneficial to maintain the temperature at a predetermined level. When there are two additions of sulphonic acid it is preferred that there are two stabilisation periods, one after each acid addition. It is preferred that the first stabilisation period is at a temperature of 40°–80° C. and most preferably 60°–70° C. and that the second and subsequent stabilisation period is at a temperature of 70°–80° C. The period of stabilisation is preferably at least 30 minutes and most preferably 1 hour, and is preferably sufficient to allow for complete neutralisation.

During the process a period of heat soaking may be beneficial after all the sulphonic acid and basic hydroxide or oxide has been added. This period allows basic salts formed during the reaction, or as a consequence of the addition of excess basic hydroxide or oxide, to be stabilised. During the heat soaking period the temperature of the reaction mixture is preferably increased, for example up to 110° C. The temperature increase is preferably linear with time and at such a rate that there is no premature water distillation from the reaction mixture. It is most preferred that the temperature is increased from 80° C. up to 110° C. over a period of at least 3 hours.

On completion of the reaction substantially all of the water present in the reaction mixture may be removed by stripping. The stripping may be carried out with a nitrogen purge to reduce the partial pressure of water vapour with increased temperature of the reaction mixture (preferably to a temperature of 150° to 160° C.), with gradual application of a vacuum or with a combination of all three.

During the process sediment may be formed which may be removed via filtration. It is preferred that sediment formation is as low as possible so that the amount of solids required to be removed is kept to a minimum and so that any filtration required can be carried out with ease and as fast as possible. The process produces products which have low sediment levels of the order of 0.5% by volume or less, preferably 0.4% or less, and high filtration rates of the order of 400 $Kgh^{-1}m^{-2}$ or greater. It is also found that the products have low haze values (which may be measured by available equipment such as a Hack haze turbidimeter) typically of the order of 6.0 NTU or less but preferably 3.0 NTU or less. During filtration a filter aid may be used, preferably a fine porosity filter aid, e.g. diatomaceous earth, Filtration may be carried out at an elevated temperature e.g. at between 150°–160° C. and under an applied pressure such as 1 to 10 bar, e.g. 8 bar.

If desired further additions of diluent oil may be made in order to obtain a desired product viscosity, content of basic sulphonate or total base number. Preferably these additions are made after filtration.

Additives such as antifoam agents may be added during the process or after filtration.

The process of the invention is illustrated by way of example only with reference to the drawing which shows a schematic flow chart illustrating the process steps for the preparation of a chloride free basic calcium sulphonate, and is further illustrated with reference to the following Examples, in which Comparative Examples 1 to 4 do not fall within the invention.

COMPARATIVE EXAMPLE 1

A mixed sulphonic acid containing $C_{24}$ alkyl benzene sulphonic acid and $C_{12}$ alkyl xylene sulphonic acid in a proportion of 2:1 (737.5 g) was dispersed in a water/diluent mixture comprising diluent mineral oil (321.7 g) and water (167.5 g) of at a temperature of approximately 25° C. This dispersion was then heated to a temperature of 50° C. and 16 g of formic acid, as an 80% by volume solution in water, was added. Calcium hydroxide of greater than 95% purity (69.0 g) was added when the temperature was at 75° C. and the temperature rose 25° C. The reaction mixture was then held at a temperature of 100° C. for 3 hours. On completion of this heat soaking stage the temperature was raised over a period of 3 hours to 160° C. to strip out the water, followed by vacuum stripping for 30 minutes at 160° C. On completion of the stripping. A diatomaceous filter aid 2.5% by mass of the reaction mixture, was added and the sulphonate filtered. The product properties are listed in Table 1.

In this example the neutralisation is undertaken in an acidic environment which produces a product with high sediment levels and slow filtration rate.

COMPARATIVE EXAMPLE 2

A mixed sulphonic acid containing $C_{24}$ alkyl benzene sulphonic acid and $C_{12}$ alkyl xylene sulphonic acid (737.5 g) was dispersed in diluent oil (382 g) with heating to 60°–65° C. Calcium chloride as a 27% by weight solution in water (27.4 g) was added to the reaction mixture followed by of formic acid solution (12.6 g); the resultant reaction mixture was stabilised at a temperature of 60°–65° C. Calcium hydroxide of greater than 95% purity (63.4 g) was added with water (88.0 g) and the temperature rose to 80°–85° C. due to the exothermic neutralisation reaction. The reaction mixture was stabilised at 80°–85° C. for 1 hour after which the reaction mixture was heat soaked by raising the temperature from 85° to 100° C. linearly over a period of 3 hours and then from 100°–110° C. in 1 hour. The heat soaked reaction mixture was then stripped of water by heating from 110° C. to 160° C. over a period of 2 hours with the application of an 850 mbar vacuum at 140° C. for 30 minutes. A diatomaceous filter aid was added at 2.0% by weight of the total reaction mixture and the reaction mixture filtered. After filtration diluent oil (70.0 g) was added plus a silicone antifoam (0.1 g). The product properties are listed in Table 1.

This example illustrates how the use of halide promoter produces high sedimentation during the manufacturing process and a product with high haze value. In addition the final product contains a significant level of halide.

COMPARATIVE EXAMPLE 3

A mixed sulphonic acid containing $C_{24}$ alkyl benzene sulphonic acid and $C_{12}$ alkyl xylene sulphonic acid (743.0 g) was dispersed in a water/diluent mixture comprising diluent oil (278.3 g) and water (151.5 g). This dispersion was heated to a temperature of 60° C. whereupon formic acid solution (16.0 g) was added and the resultant reaction mixture stabilised at a temperature of approximately 60° C. Calcium oxide (51.0 g) was added and the reaction temperature rose by 30° C. The reaction mixture was stabilised at this temperature (80° C.) for 1 hour after which time the temperature was raised to 100° C. over a period of 5 hours to heat soak the reaction mixture. The heat soaked reaction mixture was then stripped of water by heating from 100° C. to 160° C. over a period of 2 hours with application of vacuum stripping for the last half an hour. A diatomaceous filter aid 2.5% by weight was added to the stripped reaction mixture and the reaction mixture was filtered. The product properties are listed in Table 1.

This example illustrates that the addition of calcium oxide to the acid with no staged addition produces a product with high sediment and relatively high viscosity.

COMPARATIVE EXAMPLE 4

Calcium hydroxide of greater than 95% purity (68.5 g) was dispersed in a water/diluent mixture comprising diluent oil (273.0 g) and water (125.0 g) at a temperature of 60° C. Formic acid solution (18.8 g), was added at the same temperature. A mixed sulphonic acid containing $C_{24}$ alkyl benzene sulphonic acid and $C_{12}$ alkyl xylene sulphonic acid (743.0 g) was added with a resultant temperature increase of 30° C. The reaction mixture was stabilised at ~80° C. for 1 hour after which the reaction mixture was heat soaked by raising the temperature to 100° C. over a period of 5 hours. The heat soaked reaction mixture was then stripped of water by heating to 160° C. over a period of two hours with vacuum stripping for the final thirty minutes. A diatomaceous filter aid 2.5% by mass was added to the stripped reaction mixture and the mixture was filtered. The product properties are listed in Table 1.

This experiment illustrates that the addition of all the sulphonic acid to calcium hydroxide in one stage produces a product of relatively poor stability and a high haze value.

EXAMPLES 5–9

The general method for Examples 5–9 was as follows:

Calcium hydroxide (lime) of greater than 95% purity (34.3 g) was dispersed in a water/diluent mixture comprising diluent mineral oil (273 g) and water (125 g) and the resultant dispersion heated to a temperature of 20°–25° C. Formic acid solution containing 80–90% formic acid in water (in an amount of either 18.8 g or 16.0 g) was added and the temperature of the resulting reaction mixture allowed to rise to 30°–35° C. To this mixture was added a mixed sulphonic acid containing $C_{24}$ alkylbenzene sulphonic acid and $C_{12}$ alkyl xylene sulphonic acid in a proportion of 2:1 (375.15 g) with the resultant reaction causing a temperature rise to 40°–50° C. The reaction mixture was held at a temperature of 40°–50° C. for 30 mins. After this period of stabilisation a further 34.3 g of calcium hydroxide was added to the reaction mixture followed by a further addition of the mixed sulphonic acid (371.5 g); the resultant exothermic reaction raised the temperature to 70°–80° C. The reaction mixture was stabilised at this temperature for 30 mins. The mixture was then heat soaked by raising the temperature from 80° to 110° C. linearly over a period of 3 hours. On completion of heat soaking the water present in the reaction mixture was stripped by heating from 110°–160° C. linearly over a period of 2 hours with vacuum stripping for 30 mins at 160° C. and 650 mbar. A diatomaceous filter aid was added at 2.5% by mass and the product filtered. The chloride contents of all these examples was less than 50 ppm. The product properties are tabulated in Table 1 and additional experimental variables are tabulated in Table 2.

These results indicate that the process of the present invention produces basic sulphonates which have low sedimentation, low haze values, good stability, low viscosity and high filtration rates.

EXAMPLE 10

Diluent mineral oil (255.9 g) and water (110.3 g) were mixed in a reaction vessel hydrated lime of greater than 95% purity (41.3 g) was added to the water/diluent mixture and the temperature adjusted to 25°–35° C. Formic acid solution (17.9 g) containing 80–90% formic acid in water was added to the reaction vessel, the resulting temperature rise limited, by cooling, to approximately 37° C.

A mixed sulphonic acid containing $C_{24}$ alkyl benzene sulphonic acid and $C_{12}$ alkyl xylene sulphonic acid in a proportion of 2:1 (314.2 g) was added to the reaction vessel and the resulting temperature rise controlled by cooling to limit the temperature to 60°–70° C. The reaction mixture was stabilised at this temperature for 1 hour. Hydrated lime (17.7 g) was then added to the reaction mixture with stirring followed by a further addition of mixed sulphonic acid (314.2 g) and the resulting temperature rise controlled by cooling to limit the temperature to 80° C. The reaction mixture was stabilised at this temperature for 1 hour. The reaction mixture was then heated from 80°–110° C. linearly over a period of 4 hours. The reaction mixture was then heated to 160° C. linearly over a period of 2 hours in order to strip water from the mixture utilising an $N_2$ purge. At 150° C. the pressure was reduced to 400 mbar absolute over a period of 20–25 minutes and then the reaction mixture was maintained at 160° C. for a further 30 minutes or until the water content was <0.3% by mass. A diatomaceous filter aid 2.5% by mass was added to the stripped reaction product which was then filtered. A further 51.53 g of diluent oil was added to the filtered product to produce the final product. The product properties are tabulated in Table 1.

The chloride content of the final product was less than 50 ppm.

EXAMPLE 11

Calcium hydroxide of greater than 95% purity (27.75 g) was dispersed in a water/diluent mixture comprising diluent oil (312.70 g) and water (173.50 g) and the resultant dispersion was heated to a temperature of 50° C. Calcium formate (21.80 g) was added to the dispersion in the form of an aqueous solution. To this dispersion was added a mixed sulphonic acid containing $C_{24}$ alkyl benzene sulphonic acid and $C_{12}$ alkyl xylene sulphonic acid in the proportion of 2:1 (368.85 g) with the resultant reaction causing a temperature rise of 16° C. The reaction mixture was held at this temperature for 30 minutes. After this period of stabilisation the temperature of the reaction mixture was raised to 75° C. and further additions of calcium hydroxide (27.75 g) followed by mixed sulphonic (368.75 g) were made. The temperature of the reaction mixture rose by a further 16° C. to approximately 91° C. due to the heat of reaction. The reaction mixture was stabilised at this temperature for a period of 30 minutes. The mixture was then heat soaked by raising the temperature to 100° C. for a period of 3 hours. On completion of heat soaking the water present in the reaction mixture was stripped by heating the mixture to 160° C. for a period of 2 hours. A diatomaceous filter aid was added at 2.5% by mass and the product filtered.

The chloride content of the product was less than 50 ppm. The product properties are tabulated in Table 1.

EXAMPLE 12

The procedure of Example 11 was repeated with the exception that the water content of the water/diluent mixture was reduced from 173.60 g to 129.0 g.

The chloride content of the product was less than 50 ppm. The product properties are tabulated in Table 1.

Examples 11 and 12 illustrate that calcium sulphonate products with acceptable properties can be obtained by using calcium formate in place of formic acid in the process, coupled with variation of water content in the reaction mixture. The process using a higher water level (Example 11) gave superior results.

TABLE 1

| Example | Vol % Sedimentation after Water Stripping† | Filtration Rate Kgh⁻¹m⁻² | Total Base Number mg KOH g⁻¹ Concentrated | Total Base Number mg KOH g⁻¹ Diluted | Kinematic Viscosity at 100° cS | Vol % Sedimentation Initial †,‡ | Vol % Sedimentation 24 hrs Extd | Haze NTU | Colour ASTM D 1500 |
|---|---|---|---|---|---|---|---|---|---|
| 1* | 0.5 (+0.5F) | 369 | 28.9 | 28.3 | 54 | 0.01 | 0.01 (+0.4F) | — | — |
| 2* | 1.0 | 1000 | 21.5 | — | 40 | Trace | Trace | 8 | — |
| 3* | 0.5 | 538 | 28.0 | 23.8 | 68 | Trace | Trace (+0.03H) | 4.7 | — |
| 4* | 0.3 | 557 | 24.1 | — | 61 | 0.01 (0.03H) | 0.015 (+0.2H) | 7.2 | — |
| 5 | 0.5 | 438 | 30.8 | 29.2 | 53 | 0.005 (0.01H) | 0.005 (+0.02H) | 5 | D6.0 |
| 6 | 0.5 | 499 | 30.2 | — | — | Trace | Trace | 6 | 6 |
| 7 | 0.5 | 498 | 29.9 | — | 52 | Trace | 0.005 | 3.8 | 6 |
| 8 | 0.3 | 526 | 29.9 | — | 57 | Trace | — | 3 | L6.5 |
| 9 | 0.3 | 479 | 28.7 | — | 55 | Trace | — | 2.9 | 6 |
| 10 | <0.4 | — | — | 28 | 45 | <0.05 | <0.10 | 3.0 | — |
| 11 | 0.4 | 485 | 26.8 | 24.69 | 55 | Trace | 0.0075 (+0.01H) | 3.1 | — |
| 12 | 0.5 | 631 | 27 | 24.25 | 52 | Trace (+0.05H) | 0.005 (+0.5H) | 3.6 | — |

*Comparative Example
† F = flocculated fine particles
‡ H = haze

TABLE 2

|  | Example 5 | Example 6 | Example 7 | Example 8 | Example 9 |
|---|---|---|---|---|---|
| Temperature °C. (formic acid-addition) | 60 | 60 | 60 | 40 | 20 |
| Temperature °C. (2nd lime addition) | 60 | 60 | 60 | 20 | 20 |
| Temperature rise on neutralisation (°C.) | 30 | 12 | 12 | 10–12 | 10–12 |
| Soak period at 100° C. (hours) | 5 | 4 | 4 | 3 | 3 |
| Staged lime addition | No | No | No | No | Yes 1st addition 41.4 g 2nd addition 27.1 g |

We claim:

1. A method for the production of basic or neutral sulphonates comprising the addition of a sulphonic acid to a dispersion of a basic hydroxide or oxide in a water/diluent mixture to form a reaction mixture, wherein the sulphonic acid addition is made in at least two distinct stages and such that the reaction mixture remains basic throughout the addition of the acid and at least until the point of completion of the neutralisation reaction.

2. A method as claimed in claim 1 wherein the basic hydroxide or oxide is added in at least two distinct stages.

3. A method as claimed in claim 2 wherein each addition of sulphonic acid is preceded by an addition of basic hydroxide or oxide to the reaction mixture.

4. A method as claimed in claim 2 wherein the second and any subsequent addition of basic hydroxide or oxide and sulphonic acid is made at the same time.

5. A method as claimed in claim 2 wherein the first addition of basic hydroxide or oxide comprises at least 50% by weight of the total basic hydroxide or oxide.

6. A method as claimed in claim 5 wherein the first addition of basic hydroxide or oxide comprises at least 70% by weight of the total basic hydroxide or oxide.

7. A method as claimed in claim 1 wherein there is a period of stabilisation after each addition of sulphonic acid.

8. A method as claimed in claim 7 wherein the reaction mixture is at a temperature of no more than 80° C. during the period of stabilisation.

9. A method as claimed in claim 1 wherein the reaction mixture is subjected to a period of heat soaking after all the additions have been made to the reaction mixture.

10. A method as claimed in claim 1 wherein formic acid or calcium formate is added to the reaction mixture.

11. A method as claimed in claim 10 wherein the formic acid addition or the calcium formate addition precedes the first addition of sulphonic acid.

12. A method as claimed in claim 1 wherein said basic or neutral sulphonates have a kinematic viscosity at 100° C. of 65 cSt or less and a chloride content of 100 ppm or less.

* * * * *